United States Patent
Eakin

(10) Patent No.: US 7,601,143 B2
(45) Date of Patent: Oct. 13, 2009

(54) OSTOMY/FISTULA BAG

(75) Inventor: Thomas G. Eakin, Comber (GB)

(73) Assignee: T.G. Eakin Limited, Comber (GB)

( * ) Notice: Subject to any disclaimer, the term of this patent is extended or adjusted under 35 U.S.C. 154(b) by 0 days.

(21) Appl. No.: 10/568,056

(22) PCT Filed: Aug. 13, 2004

(86) PCT No.: PCT/GB2004/003520

§ 371 (c)(1),
(2), (4) Date: Jul. 13, 2007

(87) PCT Pub. No.: WO2005/016158

PCT Pub. Date: Feb. 24, 2005

(65) Prior Publication Data

US 2007/0276347 A1    Nov. 29, 2007

(30) Foreign Application Priority Data

Aug. 14, 2003    (GB) ................... 0319139.2

(51) Int. Cl.
*A61F 5/44* (2006.01)
(52) U.S. Cl. .............. 604/355; 604/174; 604/178; 604/256; 604/237; 604/317; 604/323; 604/324; 604/326; 604/327; 604/331; 604/332; 604/333; 604/337; 604/338; 604/339; 604/341; 604/350; 606/213; 606/215; 606/93; 606/94; 606/95; 606/201; 606/202; 606/203
(58) Field of Classification Search ............ 604/341, 604/350, 355
See application file for complete search history.

(56) References Cited

U.S. PATENT DOCUMENTS

| | | | | |
|---|---|---|---|---|
| 3,523,534 A | * | 8/1970 | Nolan | 604/335 |
| 3,618,606 A | * | 11/1971 | Brown et al. | 604/334 |
| 3,902,496 A | * | 9/1975 | Eakin | 604/334 |
| 4,175,563 A | * | 11/1979 | Arenberg et al. | 604/9 |
| 4,359,051 A | * | 11/1982 | Oczkowski | 604/344 |
| 4,802,474 A | * | 2/1989 | Beevers | 128/200.26 |
| 4,926,882 A | * | 5/1990 | Lawrence | 128/850 |
| 5,299,582 A | * | 4/1994 | Potts | 128/846 |
| 5,480,410 A | * | 1/1996 | Cuschieri et al. | 606/213 |
| 5,743,443 A | * | 4/1998 | Hins | 222/490 |
| 5,803,921 A | | 9/1998 | Bonadio | |
| 5,897,033 A | * | 4/1999 | Okawa et al. | 222/212 |
| 5,976,118 A | * | 11/1999 | Steer | 604/332 |
| D432,232 S | | 10/2000 | Molina | |

FOREIGN PATENT DOCUMENTS

| | | |
|---|---|---|
| EP | 0950376 A | 10/1999 |
| GB | 1131756 A | 10/1968 |
| WO | WO 95/07056 A | 3/1995 |
| WO | WO 95/27468 A | 10/1995 |

\* cited by examiner

*Primary Examiner*—Ilya Y Treyger
(74) *Attorney, Agent, or Firm*—Ungaretti & Harris LLP

(57) ABSTRACT

A lesion or fistula isolating bag, the bag defining a first chamber having a closeable entrance and a second chamber for application to a lesion or fistula and wherein access to the second chamber is made through the first chamber via a valve, the valve being arranged to inhibit passage of fluid from the second chamber to the first, and to allow said access from the first chamber to the second, the bag further comprising a closure for said closeable entrance.

17 Claims, 7 Drawing Sheets

FIG: 4A
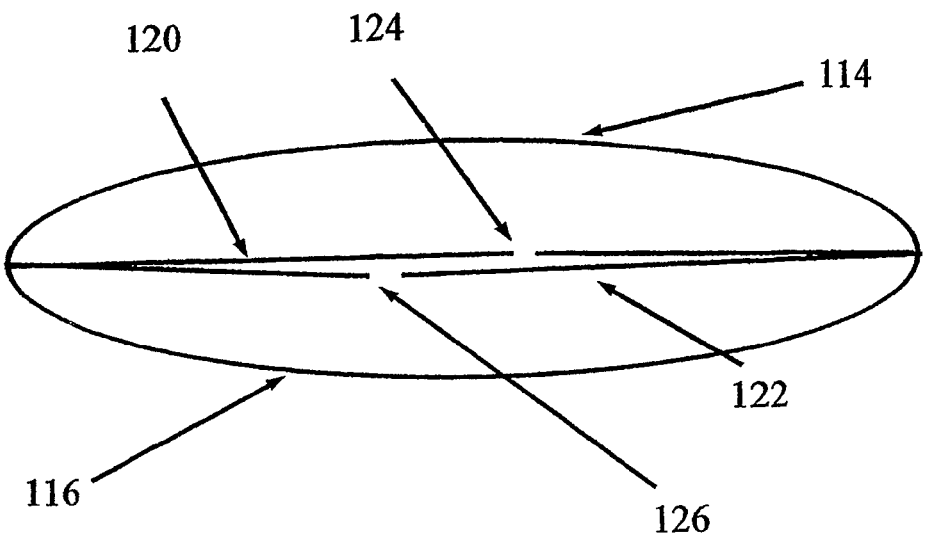
FIG: 4B
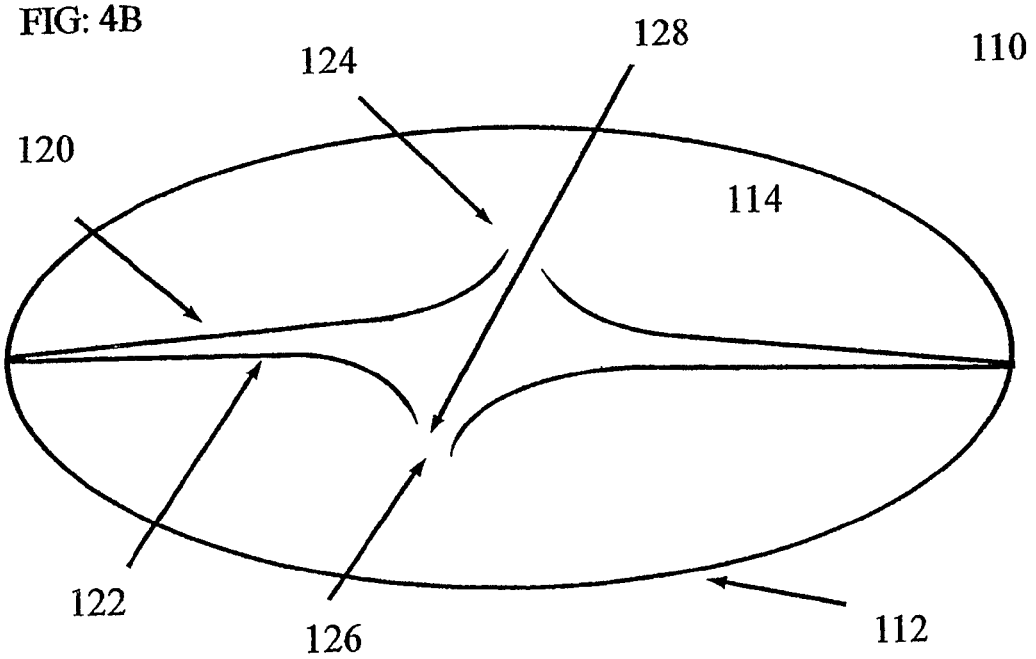

FIG: 5A
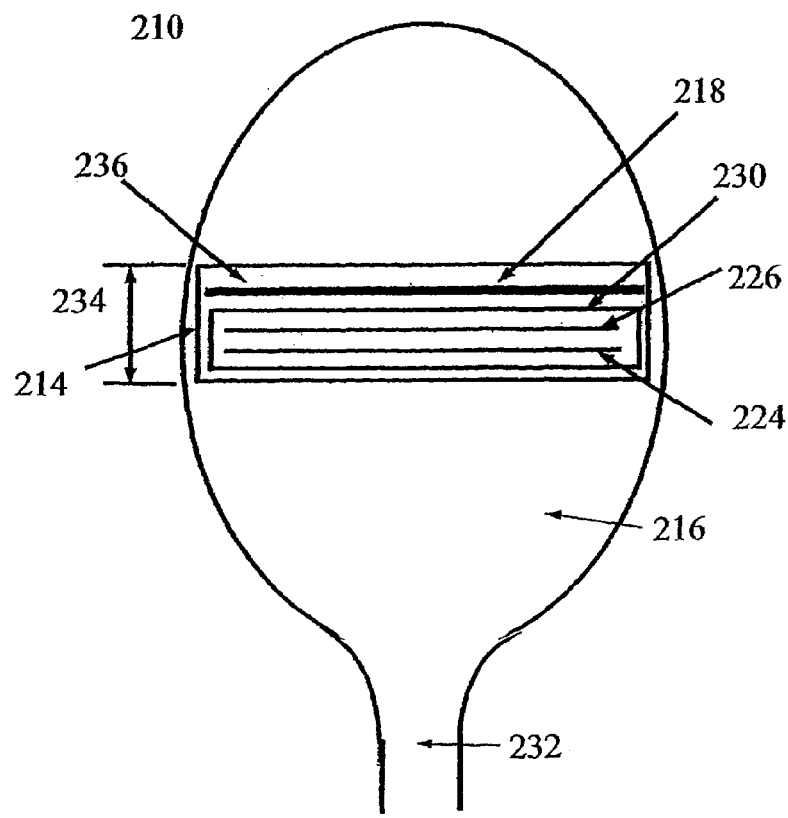
FIG: 5B
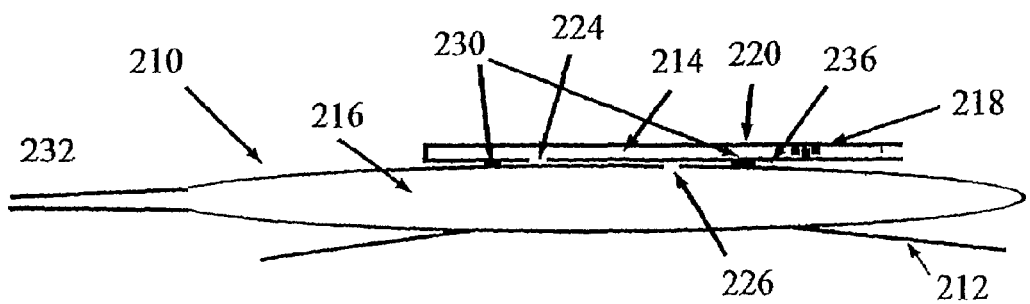

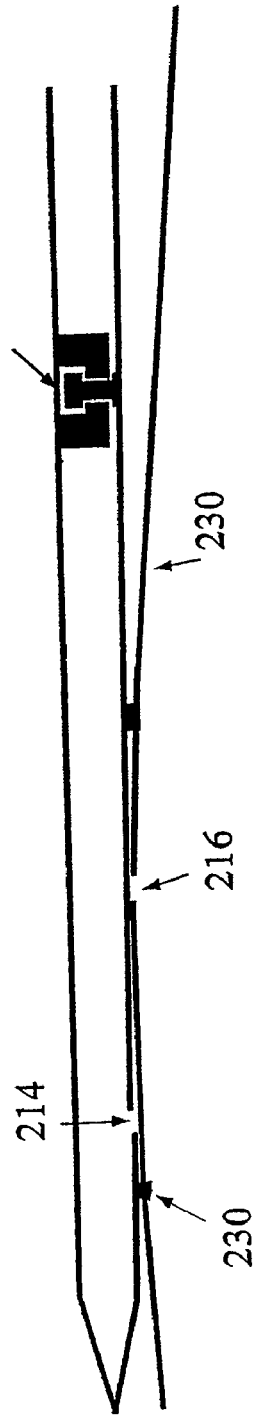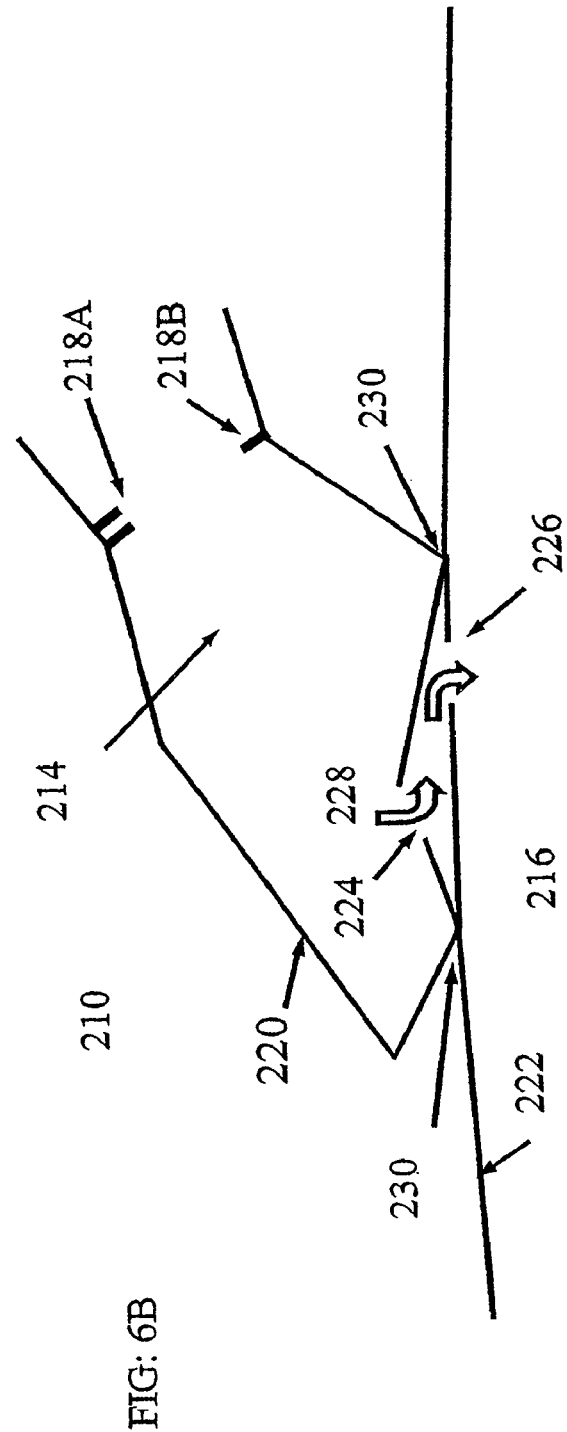
FIG: 6A
FIG: 6B

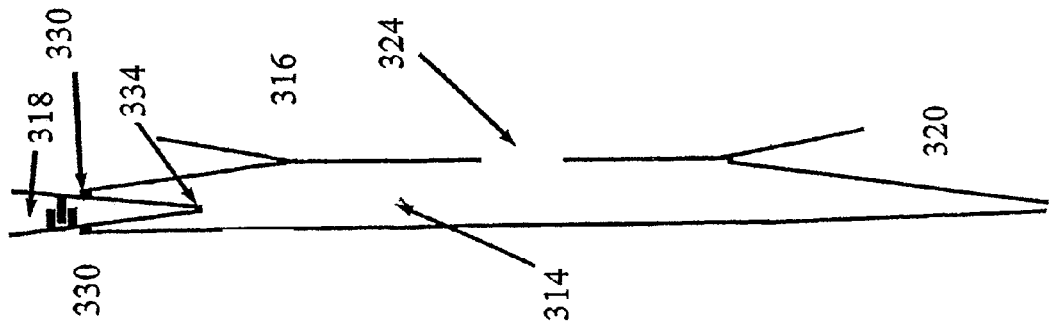
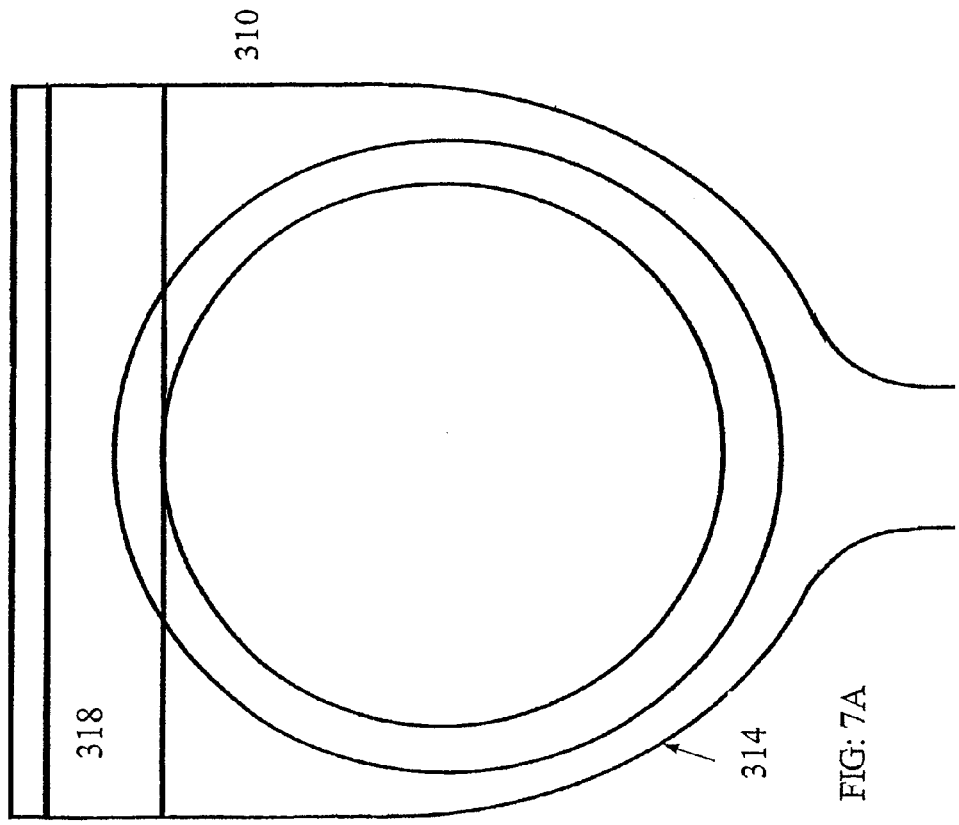

OSTOMY/FISTULA BAG

CROSS-REFERENCE TO RELATED APPLICATIONS

This Application is a U.S. National filing under § 371 of International Application No. PCT/GB2004/003520, with an international filing date of Aug. 13, 2004, now pending, claiming priority from Great Britain Application No. GB2003/19139.2, with a filing date of Aug. 14, 2003, now pending, and herein incorporated by reference.

TECHNICAL FIELD

The present invention relates to devices for providing access to a lesion—such as an ostomy or wound—or to a fistula on a person or animal (hereinafter generically referred to as a "wound") whilst isolating the wound from a surrounding environment. More specifically, the invention relates to an ostomy, fistula or wound drainage bag for this purpose.

BACKGROUND OF THE INVENTION

Various devices are known for the dressing of wounds on persons or animals which simultaneously allow access to the wound for inspection and/or for treatment whilst isolating the wound from the surrounding atmosphere. For example, a device known in the art is shown in FIG. 1. The device 10, sometimes known as a window bag, is applied to the skin of the patient 12 over the wound 18. The device consists of a body 14 which is often of generally circular cross-section and has a lid 16 which may be removably fixed to the body 14 to isolate the wound from the surrounding environment. Access to the wound may be made by removing the lid 16. These lids and bodies are of generally circular cross-section as the shape tends to allow a more efficient seal when compared to lids and bodies of other shapes.

Another type of device that is known in the art is disclosed in United States Design Pat. No. 432,232. This document discloses a wound drainage device which allows access and isolation for the wound and includes a zip fastener access for this purpose.

Such devices have several inherent disadvantages. These include the fact that the seals are not particularly efficient; i.e. the zip of US Design Pat. No. 432,232 may not be particularly water tight. Further, neither device offers efficient isolation of the wound from the surrounding atmosphere if the lid is not properly sealed.

SUMMARY OF THE INVENTION

It is an object of the present invention at least to alleviate these problems.

The invention is set out in the claims.

Embodiments of the present invention provide advantages over the prior art by providing a bag device with first and second chambers and a seal, or valve, between the chambers which inhibits the passage of fluid between the chambers but also allows access for inspection and/or treatment of the wound. In one embodiment of the present invention, this is achieved by providing two or more members which extend inside the bag from its opening and which close to form the valve. In another embodiment of the present invention, the valve is effected by providing a flexible partition which divides the chambers. Access is made to the second chamber from the first chamber through the flexible partition which has two layers, each layer having a respective slit which is offset from the other. Such an arrangement offers effectively a "zig-zag" set up which is the extra "seal" or "valve" in the device and therefore extra protection for the patient's wound. It would of course be possible to extend this arrangement so that the flexible partition has more than two layers, each layer having its own slit.

A further advantage of the present invention is that embodiments may be automatically manufactured using machinery. Many of the devices in the prior art must be manufactured by hand.

Applications of the device of the present invention include application to a wound as defined above. In such an application utilising embodiments of the present invention, the bag is fixed to a patient over a wound that he or she has. The user (a doctor or nurse) may open the bag at the entrance and enter his/her hand into the bag and the first chamber. Access can be gained to the wound for inspection and/or further treatment of the wound through the valve and the second chamber.

BRIEF DESCRIPTION OF THE DRAWINGS

Embodiments of the present invention will now be described, by way of example only, and with reference to the accompanying drawings in which:

FIGS. 4A and 4B are diagrams illustrating the manner in which the seal may be operated in the embodiment of FIG. 3;

FIGS. 5A and 5B are diagrams illustrating a further embodiment of the present invention;

FIGS. 6A and 6B are diagrams illustrating the manner in which the seal operates in the embodiment of FIG. 5 of the present invention;

FIGS. 7A and 7B show yet further embodiment of the present invention; and,

DETAILED DESCRIPTION OF THE INVENTION

Figure 1:
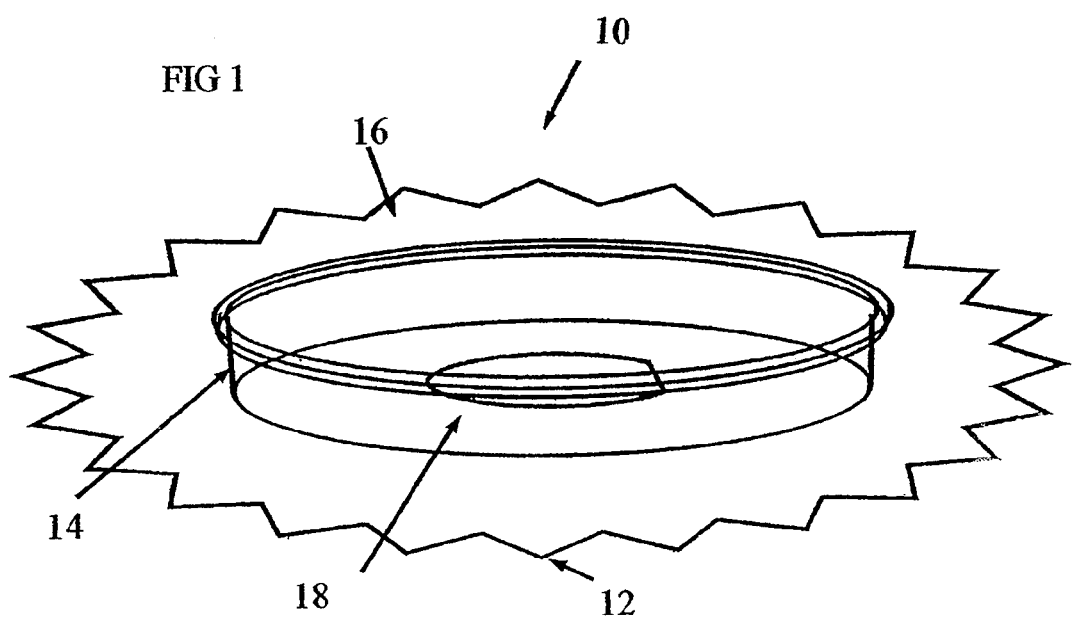
FIG. 1 is a diagram showing a window bag as known in the prior art.
Figure 2:
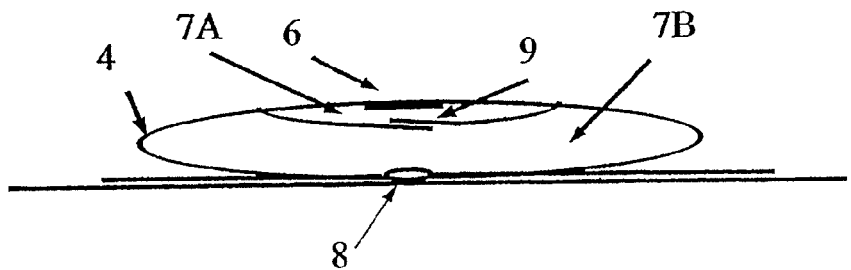
FIG. 2 is a diagram showing an embodiment of the present invention.

Referring now to FIG. 2 an embodiment of the present invention is illustrated. The bag 4 comprises an opening or entrance 6, chambers 7a and 7b and a valve 9 which isolates one chamber from the other. The bag is placed over the wound 8 of the patient 2 and the user enters his or her hand through the bag entrance 6 into the first chamber 7a. The valve 9 opens, or access is gained through it, for the user to inspect or treat the wound. Operation of the valve 9, which may take several forms, is discussed below.

Figure 3:
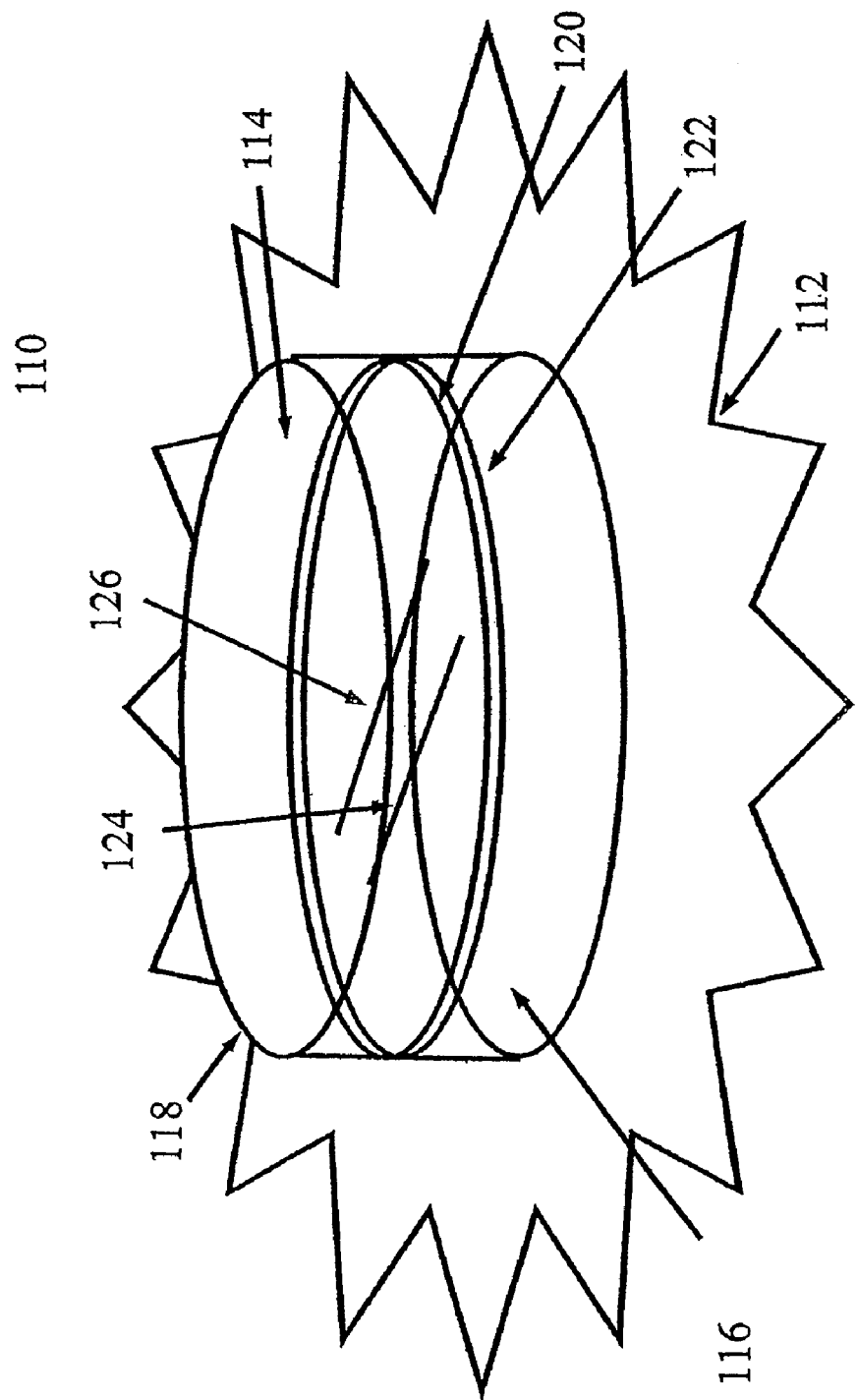
FIG. 3 is a diagram showing another embodiment of the present invention.

Referring now to FIG. 3, a device 110 according to an embodiment of the present invention is illustrated. The device 110 comprises first and second chambers 114, 116 and a closeable aperture 118 which may be provided by a lid, zip fastener or other suitable closure means. The two chambers 114, 116 are separated by a partition comprising two adjacent layers 120, 122 each of which has a respective slit 124, 126. As is illustrated, the slits may be oriented in the same direction, but offset from one another. The slits need not be parallel to one another, but may simply be oriented in substantially the same direction. It will also be appreciated that the openings in the layers need not be by means of slits, but may be by any suitable shape of opening.

In use, the device 110 is affixed to a patient's skin 112 and over a wound thereon (not shown). An outer surface of the device is adherent (for example, the outer surface may be coated in adhesive) in order to affix or attach it to a patient. Coating the outer surface of the chamber with adhesive offers a convenient and easy method of fixing the device to the patient. Preferably, the adhesive is of a type approved for medical use such that it does not irritate the patient's skin or provide any risk of infection to the wound.

In an embodiment of the invention, the first layer 120 of the partition may be heavier than the second layer 122. In this way, the forming of the seal/valve when the user's hand is withdrawn from the device is enhanced; the additional weight of the first layer of the partition presses down on the second layer such that it presses close against the patient's body thereby forming the seal. Various means may be used to achieve this additional weight in the first layer, for example, it may be formed of a material which is more dense than the material of the second layer, and/or the material of the first layer is of greater thickness than the material of the second layer.

In embodiments of the present invention the closeable aperture 118 in the first chamber is sealable, so that the aperture 118 is watertight. In other embodiments of the invention, the aperture is sealable so that it is airtight thereby increasing the sterility of the device.

In embodiments of the present invention the device is made from flexible polymer, for example, any of polyethylene (PE), polyvinyl chloride (PVC) and ethyl (or ethylene) vinyl acetate (EVA). Such polymers offer flexible and convenient-to-manufacture materials for the construction of the chambers or bag. Typically, the first layer 120 of the partition (or first chamber itself) is constructed from PE and the second layer 122 of the partition (or second chamber itself) is constructed from EVA. Other olefins or polyolefins might also be used. In this instance, PE is a slightly heavier material than EVA and, as such, assists the forming of the seal as described above.

In an embodiment of the present invention, the offset between the slits is between 15 to 30 mm. However, the offset between the slits may be between 5 mm and 100 mm or between 10 mm and 50 mm.

In an embodiment of the invention, the slits 124 and 126 are between 80 mm and 300 mm long depending on the overall size of the device. It has been found that slit lengths in this range offer convenient access without compromising the integrity of the seal offered by the partition.

Referring now to FIG. 4 the manner in which the seal operates and in which a user may gain access to a wound through the device is now discussed. FIG. 4a shows a cutaway of the device 110 illustrating the layers 120 and 122 in relation to the patient's skin 112. The wound on the patient's skin is not shown for the sake of clarity. Also shown in the first layer 120 is the slit 124 and in the second layer 122 is shown the slit 126. As mentioned above, these slits are offset from one another. The user gains access to the first chamber 114 by opening the closeable aperture 118 which is shown in FIG. 3. The user then opens the slit 124 which opens as shown in FIG. 4b as the layer is made of a flexible polymer and then accesses the opening by pushing through in the direction 128 as shown and then through the slit 126. As the second layer 122 is also made from flexible polymer, as discussed above, the user has access directly through both layers to the wound for inspection and/or treatment.

Referring now to FIG. 5, another embodiment of the present invention is now discussed. In this embodiment 210 of the device the first and second chambers are formed by the joining together of two bags or bag portions 214, 216. The two bags 214, 216 are welded together at 230 as shown in FIG. 5b. Various methods of welding may be employed for this purpose, the most suitable having been found to be thermal welding, radio-frequency welding or impulse welding.

In this embodiment, the width of the bag (dimension 234 as shown in FIG. 5a) is approximately 50 mm. A bag of this size offers sufficient width for the user to manipulate the chamber or bag to open it, and access the slits 224, 226 in order to access to the patient's wound. Of course, it will be appreciated that other dimensions of this magnitude, say between 200 and 20 mm, or between 150 and 25 mm, or 100 and 30 mm, or 75 and 40 mm may be used depending on the requirements of the particular application.

The closeable aperture 218 is formed by means of a plastic (or other suitable material) zip fastener which offers convenient closeable access to the first bag. Plastic zip fasteners on their own are inefficient at providing fluid containment, but coupled with the seal/valve offered by the flexible partition with offset slits, the device offers a secure seal to contain any fluid which may be discharged by the patient's wound.

Alternatively, and as mentioned in the preceding example, the closeable aperture is effected by a removable cover such as a lid. Any other type of closing may be used such as button fasteners, but it is preferable that the aperture is sealable.

As mentioned above, the two bags are welded together around the slits at 230. The zipper weld may be inset to allow the zipper the freedom to be opened easily by the user as shown at 236.

The width of the first bag (zipper bag) is determined such that it suits the dimensions of the second bag (wound bag).

The slit 224 in the first bag 214 should be at the bottom of the first bag while the slit 226 in the second bag 216 is situated close to the weld adjacent to the zip 214.

In embodiments of the present invention a further aperture 232 may be provided in device 210. Multiple further apertures may be provided but a single aperture 232 is illustrated for the sake of simplicity. This aperture (or apertures) may be multi-purpose in that it could be used for the draining of any fluid which is discharged by the wound, for wound irrigation or, could possibly be used for sterile access to the wound, for, for example, an intravenous drip to the patient.

The manner in which access may be effected to the patient's wound with an alternative embodiment is now illustrated in FIG. 6. The slits 224, 226 are shown in the first and second bags 214, 216. When a user inserts his or her hand through the aperture 218 (the zipper aperture 218 as shown open in FIG. 6), the action of raising the aperture 218 causes the layer 220 of the bag to move in the manner illustrated in FIG. 6b. Access may then be made to the second bag 216 in the direction 228 as shown.

FIG. 7 illustrates a further alternative embodiment of the present invention which shows an alternative version of the valve of FIGS. 3 to 6. In this embodiment the zip 318 is situated on an outside edge of the bag 314, in this case at the open top of the wound bag which is attached to the patient 316 over the wound 324. Each side of the zip strip is welded to the front and back of the bag respectively as shown at 330. The valve 334 is effected by members which extend away from the zip fastener into the bag 314 and is effective when the zip is closed. Access is obtained to the zip bag interior 314 through the open zip 318, the valve 334 so that the wound 324 may then be accessed. Such a valve which is integral with the zip 318 offers a further level of security to the device so that the likelihood of any leakage of wound discharge or of infection to the wound is greatly reduced.

As a further alternative, this valve embodiment could be used in conjunction with the valve of FIGS. 3 to 6 to provide enhanced isolation between the opening and the wound.

The aperture 320 provides a means for passage of fluid into and/or out of the bag.

Figures 8A, 8B:
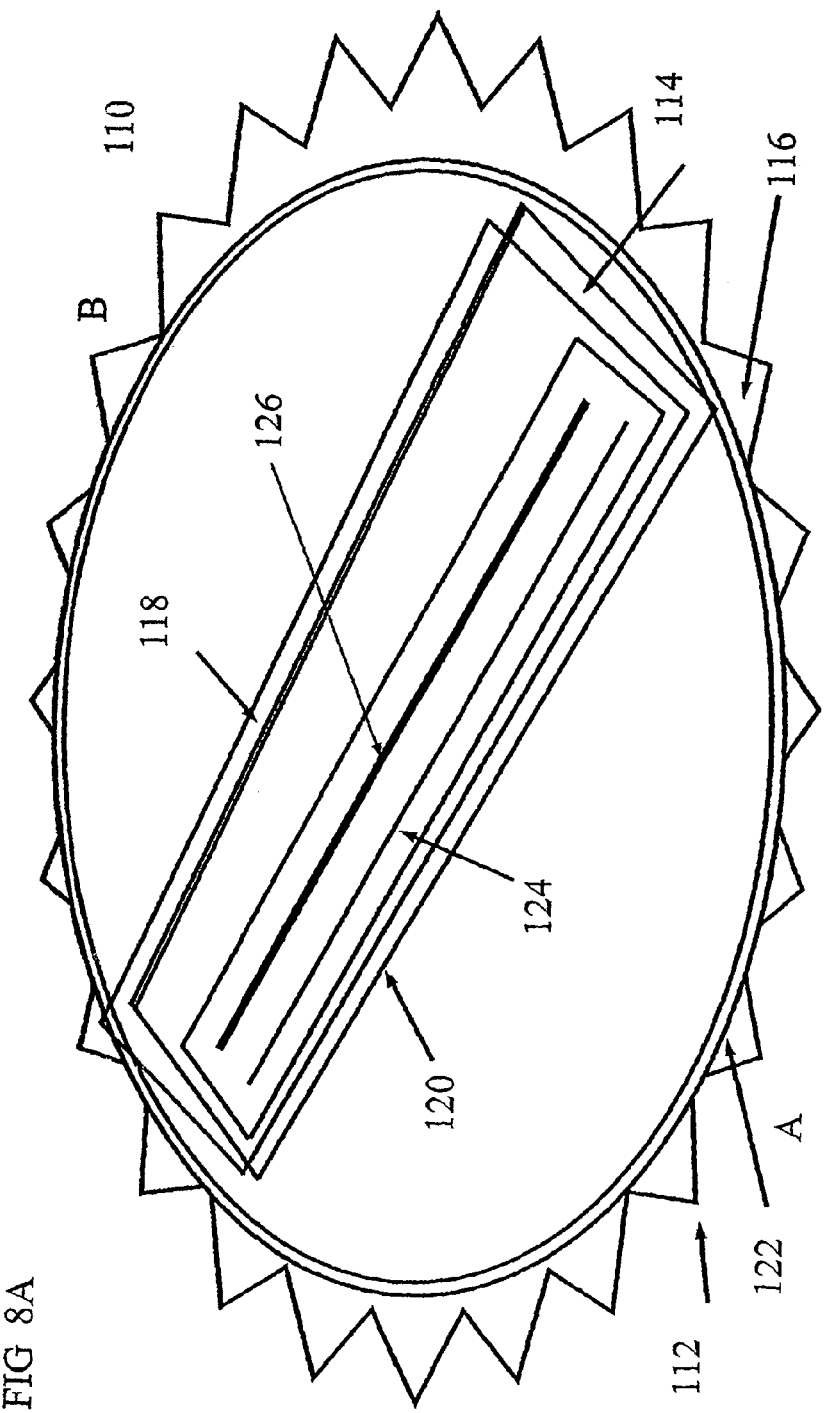
FIGS. 8A and 8B show yet other embodiments of the present invention.

Referring now to FIG. 8, a further example of an embodiment of the present invention is shown. This embodiment is a variant of the embodiment of FIG. 3, and like reference numerals refer to like parts. The device 110 of FIG. 8 comprises, again, first and second chambers 114 and 116 and a closeable aperture 118 which, in this example, is in the form of zip fastener. The two chambers 114, 116 again are separated by a partition comprising two adjacent layers 120, 122 each of which has a respective slit 124, 126. The slits may be orientated in the same direction, but offset from one another although, as mentioned above, this is not absolutely necessary; the slits may simply be oriented in substantially the same direction. Again, the openings in the layers need not be by means of slits, but may be by any suitable shape of openings. Operation of the device is as described above with reference to FIG. 3.

It will be understood that the present invention has been described above purely by way of example and modifications of detail can be made within the scope of the invention.

Each feature disclosed in the description and the claims and drawings may be provided independently or in any appropriate combination.

It will also be appreciated that features of one aspect of the invention may be applied to features of another aspect of the invention.

The invention claimed is:

1. A lesion or fistula isolating bag comprising:
  a first chamber including a closeable entrance and having a closure for sealingly closing the closeable entrance;
  a second chamber isolated from the first chamber and including means for providing access to the wound, the bag having a flexible partition isolating the second chamber from the first chamber, the flexible partition including a valve arranged to inhibit passage of fluid from the wound of the patient through the second chamber to the first chamber and to allow access to the wound of the patient from the first chamber through the second chamber, wherein the flexible partition comprises first and second adjacent layers of material, and the valve comprises portions of said first and second layers including a first aperture in the first layer and a second aperture in the second layer, said first and second apertures being oriented in substantially the same direction and being offset from one another.

2. A bag according to claim 1 in which each aperture comprises a respective slit.

3. A bag according to claim 2 in which the slits extend parallel to one another.

4. A bag according to claim 1, wherein the first layer is formed of a material which is heavier than the material of the second layer for enhancing the sealing of the valve.

5. A bag according to claim 4, wherein the material of the first layer is thicker than the material of the second layer.

6. A bag according to claim 2, wherein the offset between the slits is between 5 mm and 100 mm.

7. A bag according to claim 2, wherein the slits are between 80 and 300 mm long.

8. A bag according to claim 1, wherein the bag comprises first and second bag portions, the first chamber being formed by the first bag portion and the second chamber being formed by the second bag portion.

9. A bag according to claim 1, wherein said closeable entrance is located on an outer edge of the first chamber.

10. A bag according to claim 1, wherein the closure is a zip fastener.

11. A bag according to claim 1, wherein the closure is a removable cover.

12. A bag according to claim 1, wherein the bag includes a further aperture for the passage of fluid between atmosphere and the device.

13. A bag according to claim 12, wherein the further aperture comprises a drain.

14. A bag according to claim 1, wherein an outer surface of the second chamber is adherent.

15. A bag according to claim 1, wherein the first chamber has at least one overall dimension approximately equal to 50 mm.

16. A bag according to claim 1, wherein the bag is made from flexible polymers selected from a group consisting of polyethylene, polyvinyl chloride and ethyl vinyl acetate.

17. A bag according to claim 8, wherein there is a joint between the first and second bags and the joint is made by a welding process selected from the group consisting of thermal, radio-frequency and impulse welding.

\* \* \* \* \*